United States Patent [19]

Flanagan et al.

[11] 4,430,321
[45] Feb. 7, 1984

[54] 6-BROMOCHOLESTEROL DERIVATIVES

[75] Inventors: Richard J. Flanagan, Alberta; Leonard I. Wiebe, Edmonton, both of Canada

[73] Assignee: Merck Frosst Canada Inc., Kirkland, Canada

[21] Appl. No.: 339,265

[22] Filed: Jan. 15, 1982

[51] Int. Cl.³ .................... A61K 49/02; A61K 43/00
[52] U.S. Cl. ........................................ 424/1.1; 424/9; 260/397.2; 250/303
[58] Field of Search ............... 424/1, 1.5, 9, 1.1; 250/303; 260/397.2

[56] References Cited
U.S. PATENT DOCUMENTS 4,083,947 4/1978 Monks .................................. 250/303
4,222,887 9/1980 Matsufuji ........................ 252/299.5
4,256,727 3/1981 Triplett et al. ...................... 424/1.5

OTHER PUBLICATIONS

Fukushi, Kiyoshi, J. of Labelled Compounds and Radiopharmaceuticals, vol. XVI (1) pp. 49–51 (1979).
Kojima, M. et al., J. of Labelled Compounds and Radiopharmaceuticals, vol. XIII (2), pp. 443–451. p. 227 (1977).
Kojima, M. et al., Steroids, vol. 29, No. 4, pp. 443–451 (1977).

Primary Examiner—Benjamin R. Padgett
Assistant Examiner—M. Moskowitz
Attorney, Agent, or Firm—Thomas E. Arther; Mario A. Monaco

[57] ABSTRACT

Novel 6-bromo derivatives of cholesterol have the formula

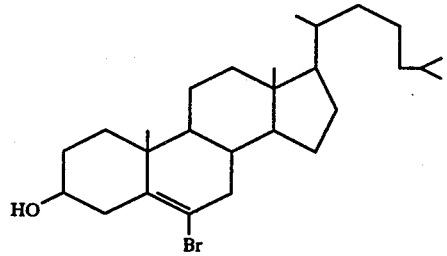

Such compounds are prepared from the known 6-iodo-cholesterol by treatment with cuprous bromide. These compounds, labelled with radioisotopes of Br-82 or Br-77, are localized in the adrenal, mammary and ovary tissue of female mammals and in the adrenal or prostate tissue of males when administered to such individuals. This provides a method for imaging adrenal, ovary or prostate tissue which is superior to use of the prior art 6-iodo-cholesterol.

8 Claims, No Drawings

6-BROMOCHOLESTEROL DERIVATIVES

BACKGROUND OF THE INVENTION

There have been reports in the scientific literature concerning the preparation of 6-iodocholesterol, radiolabelled 6-iodocholesterol and the use of such compounds in organ visualization of mammals. For example, the article "Labeling of 6-iodocholesterol with I-131" BO-Li, 3rd Int. Symp. Radiochem. St. Louis, 1980 p. 112 describes the preparation of 6-iodocholesterol labelled with I-131. The article "I-6-iodocholesterol, An Agent for Imaging the Adrenal Gland", Jixaio and Rursen, Chinese Med. Jour. 62, 237 (1979) describes the preparation of radiolabelled 6-iodocholesterol and its use as as agent which concentrates in the adrenal glands of mammals is of utility in the diagnostic investigation of adrenal gland function.

DESCRIPTION OF THE INVENTION

The present invention provides in one aspect novel 6-bromo derivatives of cholesterol and especially 6-bromocholesterol of the formula:

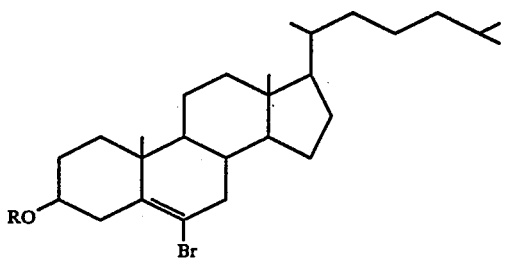

wherein R=Hydrogen or lower alkanoyl.

The invention includes compounds of the above formula and, in addition, such compounds labelled with radioactive isotopes of $^{77}Br$ or $^{82}Br$. The inactive compounds are useful aids in determining the properties of the radioactive derivatives.

The present invention also includes a method of investigating body functions of a mammal which comprises introducing into the body of a live mammal an amount of 6-bromocholesterol labelled with $^{77}Br$ or $^{82}Br$, allowing the labelled bromo compund to be localized in the mammal and then observing the radiation emitted by the labelled bromo cholesterol.

In the instance of 6-bromocholesterol it is observed that when the compound is labelled with $^{77}Br$ or $^{82}Br$ isotopes and administered to mammals and allowed to be absorbed, that the labelled 6-bromocholesterol concentrates in the adrenals mammary and ovaries of female mammals and in the adrenals and prostates of male mammals. The dosage administered to mammals is usually in the range of 0.001-0.1 m Ci/Kg of body weight. The method of introducing the 6-bromocholesterol into the mammal is the same as that used for other radiolabelled steroids and may be introduced by intravenous, intramuscular or oral administration since the ultimate localization of labelled compound is believed to be virtually independent of the route of administration.

The 6-bromocholesterol compound or the corresponding derivative labelled with $^{77}Br$ or $^{82}Br$ is prepared by the following procedure.

The known 6-iodo cholesterol is treated in solution with at least an equimolar or preferably a large molar excess of cuprous bromide optionally labelled with $^{82}Br$ or $^{77}Br$. The reaction is carried out in a solvent for the steroid, e.g., dimethyl formamide and is stirred at 25° C. for a period of 10-20 hours. The resulting 6-bromocholesterol is isolated from the resulting reaction mixture by dilution with water and extraction with chloroform. The resulting extract of product is evaporated to leave the bromocholesterol as a residue. The residue is purified by recrystallization, preferably from ethanol. If desired the 3-hydroxyl group is acylated to produce a 3-alkanoyl-6-bromo-cholesterol by treating the unacylated compound with at least one equivalent of an anhydride of an aliphatic carboxylic acid for example acetic, propionic or butyric anhydride and recovering the 3-alkanoyloxy-6-bromo-cholesterol produced.

The following examples are illustrative of our invention:

EXAMPLE I

A. The Synthesis of 6-Bromocholesterol

Cuprous Bromide (dried at 120° C., 40 mm Hg)(1.44 g., 10 mmoles) was added to a solution of 6-iodocholesterol* (512 mg, 1 mmole) in dry dimethylformamide (10 ml). The mixture was stirred at room temperature for 16 hours and then filtered to remove solids. The solution was diluted with 5% aqueous $Na_2S_2O_7$ (100 ml) and extracted with chloroform (3×20 ml). The chloroform extracts were dried over $MgSO$ and concentrated in vacuo to give an off white residue. Recrystallization from 95% ethanol gave 6-bromocholesterol as colorless needles. Yield 460 mg (99% of theoretical). M.p. 155° C.
*prepared after the manner of Levin and Shillman, JACS, 62, 920, (1940).

B. The Structure of 6-Bromocholesterol

The structural identity of the material prepared above was rigorously determined by C-13 magnetic resonance spectroscopy and proton magnetic resonance spectroscopy.

$^{13}CMR$ ($CDCl_3$, 50.32 $MH_z$, amb): 138.5(S, C-5) 120.6(S,c-6), 70.6(d, c-3), 56.3 and 56.0(2d, c-14 and c-17), 49.7(d, c-9), 43.5 (t, c-4), 42.4(S, c-13), 40.5(S, c-10) 40.1 and 39.5 and 39.4(3t, c-7, c=12 and c-24), 37.2(t, c-1), 36.2 (t, c-22), 35.8(d, c-20), 34.2(3, c-8), 31.2(t, c-2), 28.2(t, c-16), 28.0 (d, c-25), 24.1(t, c-15), 23.9(t, c-23), 22.8 and 22.6(2q, c-26 and c-27), 21.2 (t, c-11), 19.6(q, c-19), 18.7(q, c-21), 11.8(q, c-18).

PMR ($CDCl_3$, 400 $MH_z$, amb): 83.59(M, 1H, $C_3\underline{H}$—OH. $J_{3a2a}=12$, $J_{3a2e}=5.2$, $J_{3a4a}=12$, $J_{3a4e}=5.0$), 83.2(d of d, 1H, $C_4H_e$, $J_{4e7e}=2.0$, $J_{4e4a}=14.7$), 82.5(d of d of d, 1H, $C_7H_e$, $J_{7e7a}=18.5$, $J_{7e8a}=5.5$, $J_{7e4e}=2.0$).

Mass Spectroscopy (70 ev, 140° C.): 466, 464(M+, 9%), 387(34%), 386(99%), 368(41%), 352(14%), 249(12%). This evidence serves to confirm the structure of 6-bromocholesterol.

EXAMPLE II

The Labelling of 6-Bromocholesterol

A. $^{77}Br$, 6-Bromocholesterol $Na^{77}Br$ (ex MRC, Hammersmith, Init. S.A.=1 mCi/mg, 0.5 mCi), 6-iodocholesterol (1 mg, 0.002 mmoles) and cuprous iodide (1 mgm) in dry dimethylformamide (DMF) was heated at 120° C. for 8 hours. The DMF was removed in vacuo and the residue triturated with 3×1 ml of chloroform. The combined chloroform extracts were chromatographed on silica gel (50 g), using chloroform as solvent to give $^{77}$Br-6-Bromocholesterol as a single radioactive peak. Radiochemical yield 45%.

B. $^{82}$Br, 6-Bromocholesterol

Cu$^{82}$Br (ex UASF, Init. S.A.=0.8 mCi/mg, 8 mCi) and 6-iodocholesterol (4 mg, 0.008 mmoles) in dry DMF was heated at 120° C. for 16 hours. The DMF was removed in vacuo and the residue triturated with 3×1 ml of chloroform. The combined chloroform extracts were passed through a microcolumn of silica gel (20 mg) using chloroform as solvent. The entire eluate was evaporated to give the $^{82}$Br, 6-bromocholesterol as a colorless crystalline residue. Yield 3.6 mg (100% of theory).

EXAMPLE 3

Tissue Distribution of Labelled 6-Bromocholesterol

The tissue distribution measured as concentration of organ concentration/blood concentration were studied in male and female rats of the istar Strain. The selected compound was administered in solution either intravenously or orally and the animals sacrificed and dissected on the 5th day after dosing.

A. Compound of Example 1

$^{77}$Br 6-Bromocholesterol, via femoral vein injection in 1 male and 1 female rat after 5 days.

|  | Organ/blood | |
|---|---|---|
|  | Male | Female |
| liver | 1.425 | 1.537 |
| kidney | 1.017 | 1.043 |
| spleen | 2.212 | 2.239 |
| heart | 1.004 | 0.989 |
| lung | 2.937 | 3.687 |
| GIT | 0.594 | 0.705 |
| pancreas | 0.641 | 0.435 |
| blood | 1.000 | 1.000 |
| fat | 0.932 | 0.330 |
| adrenals | 24.306 | 46.957 |
| mammaries | — | 2.86 |
| ovaries | — | 2.18 |
| bladder | 1.306 | 1.38 |
| muscle | 0.467 | 0.54 |
| skin | 1.192 | 1.15 |
| uterus | — | 0.829 |
| testes | 0.410 | — |
| prostate | 14.860 | — |
| seminal vesicles | 0.520 | — |

B. Compound of Example 2

| BR-82,6BROMOCHOLESTROL IN RATS VIA ORAL INJECTION AFTER 5 DAYS | | | |
|---|---|---|---|
| FEMALE | | MALE | |
| ORGAN | ORG/BL | ORGAN | ORG/BL |
| Blood | 1.00 | Blood | 1.00 |
| Liver | 0.62 | Liver | 0.92 |
| Kidney | 0.89 | Kidney | 0.99 |
| Spleen | 2.06 | Spleen | 1.66 |
| Heart | 1.27 | Heart | 1.11 |
| Lung | 11.18 | Lung | 6.77 |
| GIT | 0.55 | GIT | 0.85 |
| Pancreas | 0.66 | Pancreas | 0.71 |
| Fat | 1.06 | Fat | 0.76 |
| Mammary | 96.03 | Testes | 0.47 |
| Adrenals | 42.43 | Adrenals | 40.87 |
| Ovaries | 7.22 | Prostate | 3.54 |
| Bladder | 7.77 | Seminal | 0.88 |
| Muscle | 1.16 | Bladder | 3.80 |
| Skin | 3.58 | Skin | 1.36 |
| Uterus | 3.74 | | |

What is claimed is:

1. A 6-bromocholesterol of the formula:

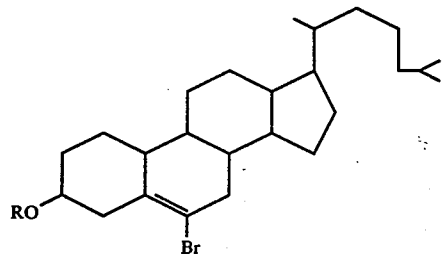

labeled with $^{77}$Br or $^{82}$Br wherein R is H or lower alkanoyl.

2. A 6-bromocholesterol compound of claim 1 comprising 6-bromocholesterol labelled with $^{77}$Br for use in the diagnostic investigation of glandular function by radiation emission.

3. A 6-bromocholesterol compound of claim 1 comprising 6-bromocholesterol labelled with $^{82}$Br for use in the diagnostic investigation of glandular function by radiation emission.

4. A method of investigative diagnosis which comprises introducing into a live mammal a 6-bromocholesterol compound of claim 1 labelled with $^{77}$Br or $^{82}$Br and subsequently observing the radiation localized in individual glands of said mammals.

5. A method as claimed in claim 4 wherein the part of the mammal to be investigated is the adrenal glands.

6. A method as claimed in claim 4 wherein the part of the mammal to be investigated is the prostate gland.

7. A method as claimed in claim 4 wherein the part of the mammal to be investigated is the mammary gland.

8. A method as claimed in claim 4 wherein the part of the mammal to be investigated is the ovary.

* * * * *